(12) United States Patent
Renati et al.

(10) Patent No.: US 7,115,138 B2
(45) Date of Patent: Oct. 3, 2006

(54) SHEATH TIP

(75) Inventors: Richard J. Renati, Los Gatos, CA (US); Jackson F. Demond, Santa Cruz, CA (US); Jeff A. Krolik, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 215 days.

(21) Appl. No.: 10/234,260

(22) Filed: Sep. 4, 2002

(65) Prior Publication Data

US 2004/0044359 A1   Mar. 4, 2004

(51) Int. Cl.
*A61M 29/00* (2006.01)
(52) U.S. Cl. .................................. 606/200; 606/127
(58) Field of Classification Search ................ 606/191, 606/194, 200, 127; 604/263, 264
See application file for complete search history.

(56) References Cited

U.S. PATENT DOCUMENTS

| 3,472,230 | A | 10/1969 | Fogarty |
| 3,952,747 | A | 4/1976 | Kimmell, Jr. |
| 3,996,938 | A | 12/1976 | Clark, III |
| 4,023,559 | A | 5/1977 | Gaskell |
| 4,046,150 | A | 9/1977 | Schwartz et al. |
| 4,425,908 | A | 1/1984 | Simon |
| 4,590,938 | A | 5/1986 | Segura et al. |
| 4,619,246 | A | 10/1986 | Molgaard-Nielsen et al. |
| 4,650,466 | A | 3/1987 | Luther |
| 4,706,671 | A | 11/1987 | Weinrib |
| 4,723,549 | A | 2/1988 | Wholey et al. |
| 4,790,812 | A | 12/1988 | Hawkins, Jr. et al. |
| 4,790,813 | A | 12/1988 | Kensey |
| 4,794,928 | A | 1/1989 | Kletschka |
| 4,807,626 | A | 2/1989 | McGirr |
| 4,863,424 | A | 9/1989 | Blake, III et al. |
| 4,873,978 | A | 10/1989 | Ginsburg |
| 4,921,478 | A | 5/1990 | Solano et al. |
| 4,921,484 | A | 5/1990 | Hillstead |
| 4,926,858 | A | 5/1990 | Gifford, III et al. |
| 4,969,891 | A | 11/1990 | Gewertz |
| 4,998,539 | A | 3/1991 | Delsanti |
| 5,002,560 | A | 3/1991 | Machold et al. |
| 5,011,488 | A | 4/1991 | Ginsburg |
| 5,053,008 | A | 10/1991 | Bajaj |
| 5,071,407 | A | 12/1991 | Termin et al. |
| 5,100,423 | A | 3/1992 | Fearnot |
| 5,102,415 | A | 4/1992 | Guenther et al. |
| 5,133,733 | A | 7/1992 | Rasmussen et al. |
| 5,152,771 | A | 10/1992 | Sabbaghian et al. |
| 5,152,777 | A | 10/1992 | Goldberg et al. |
| 5,160,342 | A | 11/1992 | Reger et al. |

(Continued)

FOREIGN PATENT DOCUMENTS

DE   28 21 048   7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Michael J. Hayes
*Assistant Examiner*—Michael G. Mendoza
(74) *Attorney, Agent, or Firm*—Crompton, Seager & Tufte LLC

(57) ABSTRACT

An embolic protection filter delivery and/or retrieval assembly. In one embodiment the assembly includes a shaft having a filter coupled thereto, a sheath, and a tapering member.

9 Claims, 4 Drawing Sheets

U.S. PATENT DOCUMENTS

| | | |
|---|---|---|
| 5,224,953 A | 7/1993 | Morgentaler |
| 5,329,942 A | 7/1994 | Gunther et al. |
| 5,330,484 A | 7/1994 | Gunther |
| 5,354,310 A | 10/1994 | Garnie et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,015,423 A * | 1/2000 | Andrese .................... 606/198 |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,596,011 B1 * | 7/2003 | Johnson et al. ............. 606/200 |
| 6,761,703 B1 * | 7/2004 | Miller et al. ............. 604/96.01 |
| 2002/0111649 A1 * | 8/2002 | Russo et al. ................ 606/200 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| EP | 1 232 756 A2 | 8/2002 |
| EP | 1232765 A2 * | 8/2002 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |

| | | |
|---|---|---|
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |
| WO | WO 02/062407 A2 | 8/2002 |

OTHER PUBLICATIONS

"Endovascular Grafts, Stents Drive Interventional Radiology Growth," Cardiovascular Device Update, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," AJR, 141:601-604 (Sep. 1983).

Cragg, Andrew et al., "Nonsurgical Placement of Arterial Endoprosthesis: A New Technique Using Nitinol Wire," AJR, pp. 261-263 (Apr. 1983).

Diethrich et al., "Percutaneous Techniques for Endoluminal Carotid Interventions," J. Endovasc. Surg., 3:182-202 (1996).

Fadali, A. Moneim, "A filtering device for the prevention of particulate embolization during the course of cardiac surgery," Surgery, 64(3):634-639 (Sep. 1968).

Haissaguerre et al., "Spontaneous Initiation of Atrial Fibrillation by Ectopic Beats Originating in the Pulmonary Veins," The New England Journal of Medicine, 339(10):659-666 (Sep. 1988).

Jordan, Jr. et al., "Microemboli Detected by Transcranial Doppler Monitoring . . . ," Cardiovascular Surgery, 7(1)33-38 (Jan. 1999).

Lesh, "Can Catheter Ablation Cure Atrial Fibrillation?" ACC Current Journal Review, pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ," American Heart Journal, 125(2 Pt 1):362-366 (Feb. 1993).

Mazur et al., "Directional Atherectomy with the Omnicath™: A Unique New Catheter System," Catheterization and Cardiovascular Diagnosis, 31:17-84 (1994).

Moussa, MD, Issaam "Stents Don't Require Systemic Anticoagulation . . . But the Technique (and Results) Must be Optimal," Journal of Invasive Cardiol., 8(E):3E-7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," Cardiovascular & Interventional Radiology, 21(5):386-392 (1998).

Theron et al., "New Triple Coaxial Catheter System for Carotid Angioplasty with Cerebral Protection," American Journal of Neuroradiology, 11:869-874 (1990).

Tunick et al., "Protruding atherosclerotic plaque in the aortic archo f patients with systemic embolization: A new finding seen by transesophageal echocardiography," American Heart Journal 120(3):658-660 (Sep. 1990).

Waksman et al., "Distal Embolization is Common After Directional Atherectomy . . . ," American Heart Journal, 129(3):430-435 (1995).

Wholey, Mark H. et al., PTA and Stents in the Treatment of Extracranial Circulation, The Journal of Invasive Cardiology, 8(E):25E-30E (1996).

* cited by examiner

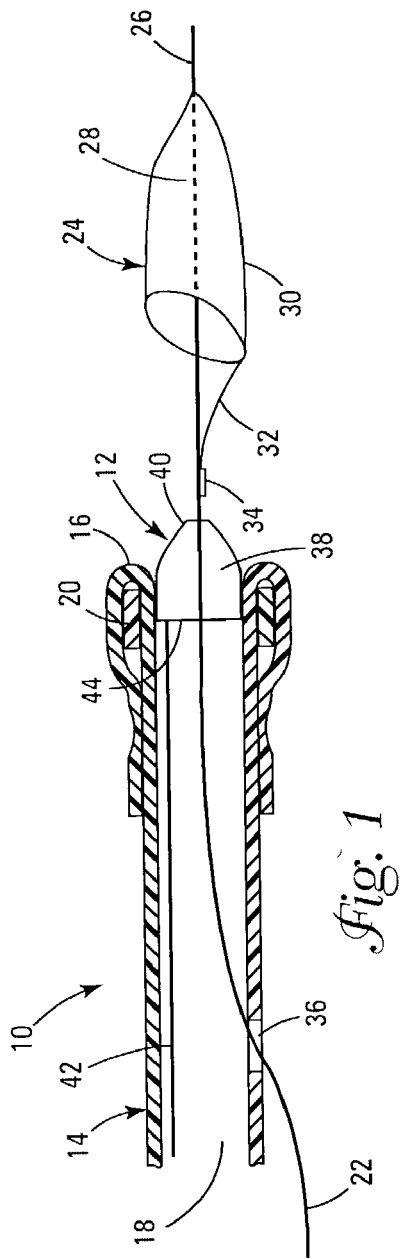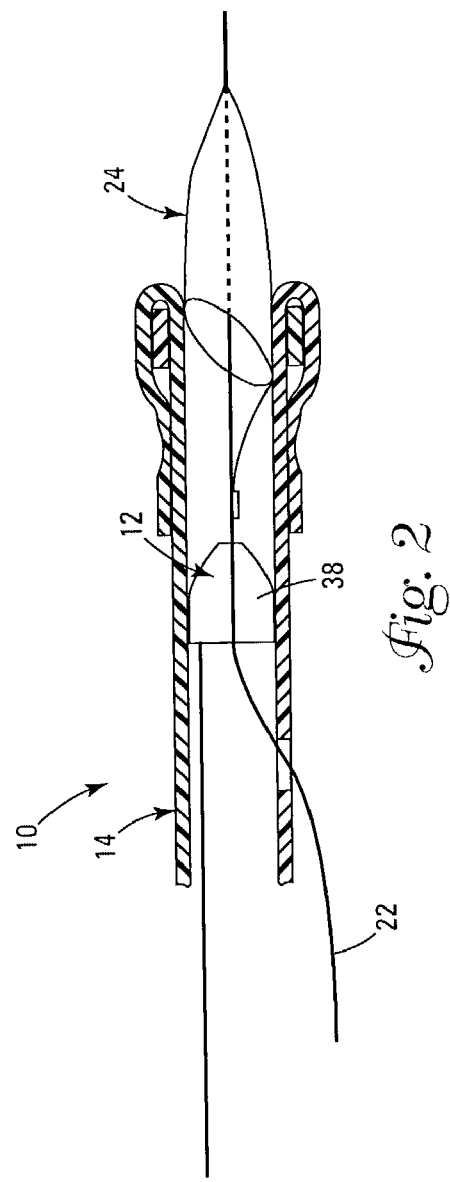

SHEATH TIP

FIELD OF THE INVENTION

The present invention pertains to devices for filtering debris from a body lumen. More particularly, the present invention pertains to devices for delivering and retrieving embolic filtering devices.

BACKGROUND

Heart and vascular disease are majors problem in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

Brief Summary of the Invention The present invention incorporates design and manufacturing refinements to embolic protection devices. In some embodiments, the present invention includes an embolic protection filter delivery and/or retrieval assembly. The assembly includes a shaft or guidewire having a filter coupled thereto, a sheath, and a tapering member.

BRIEF DESCRIPTION OF THE DRAWINGS

FIG. 1 is a partial cross-sectional view of an example embolic protection delivery and/or retrieval assembly;

FIG. 2 is a partial cross-sectional view of the assembly of FIG. 1, wherein an embolic protection filter is disposed within the sheath;

DETAILED DESCRIPTION

Figure 3:
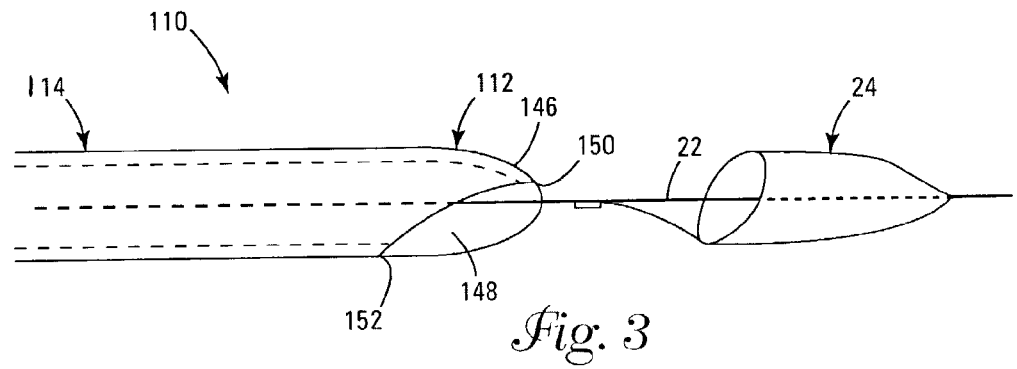
FIG. 3 is an overview of another example of an embolic protection delivery and/or retrieval assembly.

The following description should be read with reference to the drawings wherein like reference numerals indicate like elements throughout the several views. The detailed description and drawings illustrate example embodiments of the claimed invention.

A number of embolic protection devices exist that filter embolic debris generated during an intravascular intervention. Delivering and retrieving the filter often includes the use of a catheter or sheath that is advanced to an appropriate location adjacent, for example, an intravascular lesion. In some cases, the lesion may be expanded with a stent and the delivery or retrieval sheath may need to pass the stent. Thus, it may be desirable for the sheath to have a tapered or rounded tip so as to more easily pass the stent without "catching" or otherwise displacing the stent. The present invention includes several examples of a filter delivery and/or retrieval assembly 10 that includes a tapering member 12 coupled to a delivery and retrieval sheath 14. Tapering member 12 may be adapted and configured to provide assembly 10 (i.e., sheath 14) with a generally tapered or rounded distal end that may, for example, allow assembly 10 to more easily pass an intravascular stent.

Assembly 10 includes a sheath 14 which may be a delivery or retrieval catheter and includes a proximal end (not shown), a distal end 16, and a lumen 18 extending therethrough. Sheath 14 may be comprised of a metal, metal alloy, polymer, metal-polymer composite, or any other suitable material. Some examples of suitable polymers include polyurethane, polyether-ester (for example a polyether-ester elastomer such as ARNITEL® available from DSM Engineering Plastics), polyester (for example a polyester elastomer such as HYTREL® available from DuPont), or linear low density polyethylene (for example REXELL®), and the like, or copolymers or mixtures or combinations thereof. Additionally, sheath 14 may be made of polymers such as polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene, Marlex high-density polyethylene, and the like, or mixtures, combinations, or copolymers thereof, or with any of the other materials listed above. Polyamides, for example, are particularly suitable for providing a relatively rigid sheath 14. Some other suitable materials for a rigid tubular member include polyetheretherketone (PEEK), polyimide (PI), and polyetherimide (PEI). PEBA, in contrast to the rigid polyamides, is a relatively flexible polymeric material. The use of a polyamide can impart a slightly less rigid durometer than the rigid polyamides and slightly greater than the flexible PEBA material.

In some embodiments, sheath 14 may be a single polymer, multiple layers, or a blend of polymers. In some embodiments sheath 14 can include a liquid crystal polymer (LCP) blended with other polymers to enhance torqueability. By employing careful selection of materials and processing techniques, thermoplastic, solvent soluble, and thermosetting variants of these and other materials can be employed to achieve the desired results.

Additionally, in some embodiments, a coating, for example a lubricious (e.g., hydrophilic) or other type of coating may be applied over portions or all of sheath 14, and/or other portions of assembly 10. Hydrophobic coatings such as fluoropolymers, including polytetrafluroethylene (PTFE), provide a dry lubricity which improves guidewire handling and device exchanges. Lubricious coatings improve steerability and improve lesion crossing capability. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

A marker member 20 may be disposed adjacent distal end 16 of sheath 14. Marker member 20 may comprise a marker band, coil, or other suitable structure that is at least partially comprised of radiopaque materials. Radiopaque materials are understood to generally produce a relatively bright image on a fluoroscopy screen during a medical procedure. This relatively bright image aids the user of assembly 10 in determining its location. Radiopaque materials include, but are not limited to, gold, platinum, and plastic material loaded with a radiopaque filler. In some embodiments, marker member 20 can be disposed adjacent distal end 16 of sheath 14 by coupling marker member 20 to sheath 14 and then proximally folding back a portion of sheath 14 over marker member 20.

An elongate shaft or filter guidewire 22 can be disposed within at least a portion of lumen 18 of sheath 14. Shaft 22 can be made of any suitable material including metals, metal alloys, polymers, or the like, or combinations or mixtures thereof. Some examples of suitable metals and metal alloys include stainless steel, such as 304v stainless steel; nickel-titanium alloy, such as nitinol, nickel-chromium alloy, nickel-chromium-iron alloy, cobalt alloy, or the like; or other suitable material. The entire shaft 22 can be made of the same material, or in some embodiments, can include portions or sections made of different materials. In some embodiments, the material used to construct shaft 22 is chosen to impart varying flexibility and stiffness characteristics to different portions of shaft 22. For example, the material used to construct a proximal region can be relatively stiff for pushability and torqueability (e.g., straightened 304v stainless steel wire), and the material used to construct a distal region can be relatively flexible by comparison for better lateral trackability and steerability (e.g., a straightened super elastic or linear elastic alloy such as nickel-titanium wire).

In some embodiments, shaft 22 may extend through a portion of lumen 18 and exit sheath 14 at a port 36. Port 36 is disposed relatively near distal end 16 of sheath 14 and allows a single operator to exchange catheters (or assemblies such as assembly 10) over shaft 22. Alternatively, shaft 22 may extend proximally through essentially the entire length of lumen 18. According to this embodiment, catheter exchanges occur by removing the first catheter and then advancing the second catheter over-the-wire.

An embolic protection filter 24 is coupled to shaft 22, for example near a distal end 26 thereof, however, it can be appreciated that filter 24 could be disposed at essentially any position along shaft 22. Filter 24 may generally comprise a filter material 28 disposed over a filter frame 30, and one or more struts 32. In general, filter 24 operates between a first generally collapsed configuration and a second generally expanded configuration for collecting debris in a body lumen. Frame 30 may be comprised of a "self-expanding" shape-memory material such as nickel-titanium alloy (to bias filter 24 to be in the second expanded configuration). Filter material 28 may be comprised of, for example, a polyurethane sheet and include at least one opening that may be, for example, formed by known laser techniques. The holes or openings are sized to allow blood flow therethrough but restrict flow of debris or emboli floating in the body lumen or cavity. Strut 32 may be coupled to shaft 22 by a coupling 34. Coupling 34 may be one or more windings of strut 32 about shaft 22 or be a fitting disposed over an end of strut 32 to attach it to shaft 22.

In some embodiments, tapering member 12 may include a nose cone 38 as illustrated in FIG. 1. Nose cone 38 includes a tapered distal end 40 and may be slidably disposed within lumen 18. According to this embodiment, nose cone 38 may be adapted to shift between a first position, wherein at least a portion of nose cone 38 (e.g., distal end 40) extends beyond distal end 16, and a second position, wherein nose cone 38 is retracted proximally. It can also be appreciated that in some embodiments, nose cone 38 may be removable from sheath 14 by retracting nose cone 38 proximally.

It can be appreciated that when nose cone 26 is in the first position, that it provides distal end 16 of sheath 14 with a generally tapered or rounded surface. This tapered surface may, for example, help assembly 10 pass a stent without displacing the stent. The tapered surface may also help assembly 10 pass other areas, for example areas narrowed by thrombus, a medical device, a lesion, plaque, and the like.

An actuating member 42 may be coupled to nose cone 38, for example at a proximal position 44 thereof. Actuating member 42 may comprise a shaft that extends from proximal position 44 to a proximal location where it is accessible to a user (directly or indirectly). Thus, actuating member 42 may be actuated by the user so that movement thereof translates to essentially analogous movement of nose cone 38.

In at least some embodiments, actuation of actuating member 42 may result in nose cone 38 shifting between the first position and the second position. For example, actuating member 42 may be advanced distally to place nose cone 38 in the first position. According to this embodiment, actuating member 42 is comprised of a sufficiently stiff material so as to allow actuating member 42 to exert a force onto nose cone 38 that is sufficient to distally advance nose cone 38 within lumen 18. In some embodiments, the inside surface of sheath 14 is sufficiently lubricous so that the required force is relatively low and, thus, actuating member 42 need only be minimally stiff.

Alternatively or in addition to what is described above, nose cone 38 may be predisposed in the first position and advanced through the vasculature. Upon reaching filter 24, actuating member 42 may be urged in the proximal direction to shift nose cone 38 to the second position. According to this embodiment, actuating member 42 may be comprised of a flexible material so as to allow assembly 10 (particularly the distal portion of assembly 10) to maintain the desired flexibility. It can be appreciated that the flexibility of actuating member 42 can be altered without departing from the spirit of the invention.

When assembly 10 is used to retrieve filter 24, nose cone 38 may be configured in the first position as shown in FIG. 1. Assembly 10 may then be passed over shaft 22 and advanced to a position adjacent filter 24. Nose cone 38 may then be shifted to the second position as shown in FIG. 2 (for example, by proximally urging actuation member 42). Shifting nose cone 38 to the second position allows sheath 14 to be advanced distally over filter 24 so that filter 24 can become disposed within lumen 18. Assembly 10 (and, thus, filter 24) can then be removed from the vasculature.

FIG. 3 is an overview of another example filter delivery and/or retrieval assembly 110 that is essentially the same in form and function as assembly 10, except that tapering member 112 comprises a streamlined or rounded distal head 146 having a mouth or opening 148. It can be appreciated that assembly 110 may be used for either delivery or retrieval of filter 24. Distal head 146 may be attached to, integral with, or otherwise coupled to sheath 14 and provides assembly 110 with a generally tapered distal end. Mouth 148 may be configured so that it opens in a direction oriented at an angle relative to the general direction of lumen 18. More precisely, mouth 148 may point in a direction that is skewed relative to the longitudinal axis of sheath 114 (and/or lumen 118).

The skew of mouth 148 is embodied by the location of a first terminus 150 and a second terminus 152 of mouth being horizontally spaced. More particularly, first terminus 150 is located distally of second terminus 152. This configuration differs from a typical, blunt ended tube where the corresponding first terminus and second terminus would be oriented in the same vertical plane (i.e., both termini located at essentially the same longitudinal position). By skewing the orientation of mouth 148, mouth 148 can be sized so as to allow filter 24 to become disposed within sheath 114 while maintaining a generally tapered or rounded distal tip. Moreover, the size of mouth 148 can be altered by manipulating the position of second terminus 152 during manufacturing of assembly 110.

Figure 4:
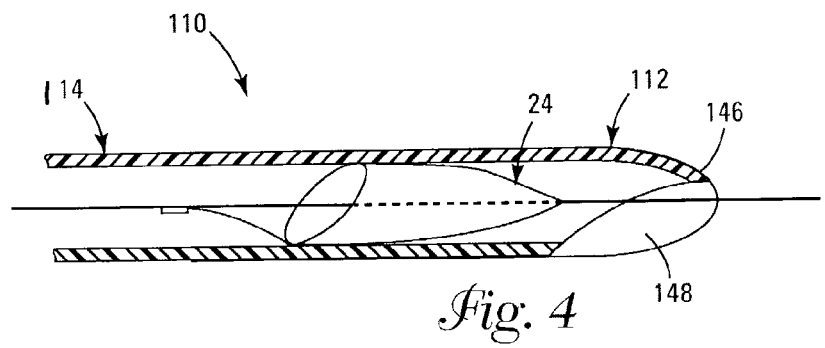
FIG. 4 is a partial cross-sectional view of the assembly of FIG. 3, wherein an embolic protection filter is disposed within the sheath.

Assembly 110 (more particularly, sheath 114) can be advanced over shaft 22 so as to dispose filter 24 within lumen 18 as shown in FIG. 4. This allows assembly 110 to be used to retrieve filter 24. In some embodiments skewing mouth 148 may allow the outside diameter to be smaller than that of typical filter retrieval catheters. This provides assembly 110 with the ability to be used in medical interventions that require smaller medical devices. For example, assembly 110 may be used to access the neurological vasculature and other remote locations.

When using assembly 110 to deliver filter 24, filter 24 can be disposed within lumen 18 (e.g., by backloading filter 24 into lumen 18 such that filter 24 is generally collapsed within sheath 114). Assembly 110 can then be advanced through the vasculature to a location adjacent an area of interest. Sheath 114 can then be retracted proximally such that filter 24 emerges from distal end 16 of sheath 114. Sheath 114 may then shift to the expanded configuration suitable for filtering embolic debris.

Figure 5:
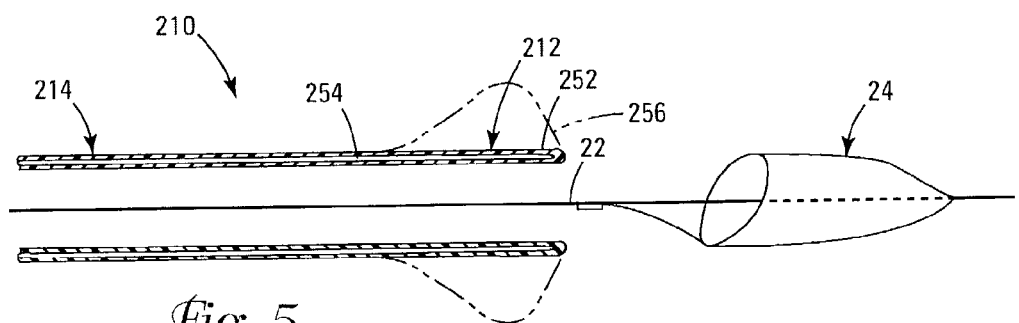
FIG. 5 is a partial cross-sectional view of another example of an embolic protection delivery and/or retrieval assembly.

FIG. 5 is a partial cross-sectional view of another example delivery and/or retrieval assembly 210 that is essentially the same in form and function as assembly 10, except that tapering member 212 comprises an bulbous tip 252. In some embodiments, bulbous tip 252 is inflatable. Additionally, assembly 210 may include an alternate sheath 214 that is essentially the same as sheath 14 except that sheath 214 includes an inflation lumen 254 in fluid communication with bulbous tip 252.

Bulbous tip 252 includes a tapered leading surface 256 that provides assembly 210 with a generally tapered distal end when in the first position. In some embodiments, tapered member 212 is in the first position when bulbous tip 252 is inflated or otherwise in the expanded configuration. Like the other examples described above, leading surface 256 allows assembly 210 to more easily pass through, for example, a stent without catching and/or displacing the stent.

Figure 6:
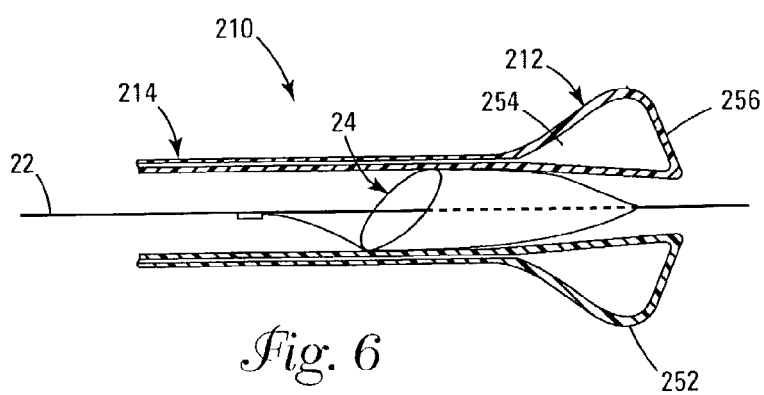
FIG. 6 is a partial cross-sectional view of the assembly of FIG. 5, wherein an embolic protection filter is disposed within the sheath.

FIG. 6 also illustrates bulbous tip 252 in an inflated or bulbous configuration. In some embodiments bulbous tip 252 may be constitutively inflated or generally configured in the bulbous shape. According to this embodiment, bulbous tip 252 may comprise a generally solid material or a non-solid material that elastically retains its shape. It can be appreciated that a number of different materials can be utilized to result in the desired shape or properties of bulbous tip 252. Substitution of these different materials are thought to be within the scope of the invention.

Figure 7:
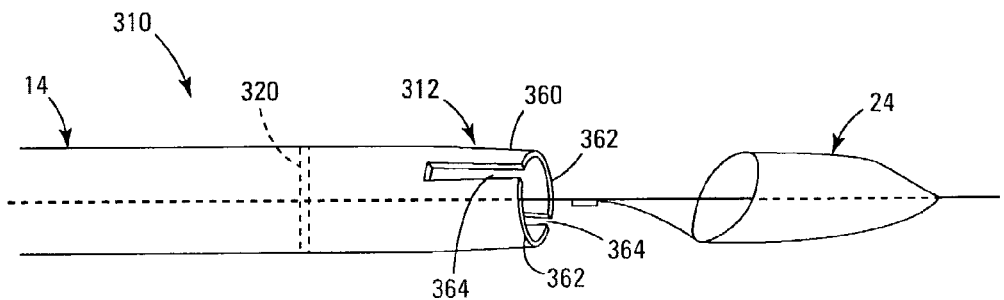
FIG. 7 an overview of another example of an embolic protection delivery and/or retrieval assembly.

FIG. 7 is an overview of another example delivery and retrieval assembly 310. Assembly 310 is essentially the same in form and function as assembly 10, except that tapering member 312 includes a notched tip 360. Notched tip 360 may be comprised of a generally flexible material and may taper distally. The distal taper of notched tip 360 provides assembly 310 with a tapered distal end that may be desirable as described above.

Assembly 310 may also include one or more marker members 320. In some embodiments, marker member 320 may be coupled to shaft 14 essentially the same as marker member 20 (i.e., sheath 14 may be folded back proximally over marker member 320). Alternatively, marker member 320 may be coupled to the exterior or interior surface of sheath 14, or otherwise encapsulated within sheath 14. Moreover, marker member 320 may be disposed at essentially any position along the length of sheath 14. For example, marker member 320 may be disposed about 4 millimeters or less from distal end 16 of sheath 14.

Figure 8:
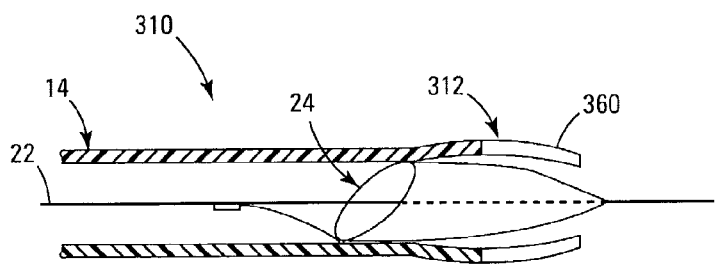
FIG. 8 is a partial cross-sectional view of the assembly of FIG. 7, wherein an embolic protection filter is disposed within the sheath.

Notched tip 360 includes a plurality of segments 362 separated by one or more notches 364. In some embodiments, assembly 310 includes two segments 362 and two notches 364. However, it can be appreciated that the number of segments 362 and notches 364 may be altered without departing from the spirit of the invention. In general, notches 364 provide space so that segments 362 can taper inward when in the first position (i.e., configured for advancing through the vasculature and, for example, passing a stent) and expand or widen when in the second position (i.e., configured for having filter 14 disposed therein) as shown in FIG. 8. In some embodiments, segments 362 may be biased to taper inward and, thus, be biased to be in the first position.

It can also be appreciated that increasing the depth or length of notches 364 may allow tapering member 312 to have a smaller profile and/or be more tapered. Moreover, increasing the length of notches 364 may enhance the stent crossing ability of assembly 310. The length of notches 364 are defined by the distance in the proximal direction that notches 364 extend to. Some embodiments of the invention includes notches 364 with a relatively enhanced length in order to accommodate applications where a smaller profile would be desirable. For example, the length of notches 364 may be about 1 to about 4 millimeters or less for these applications. Alternative embodiments include notches 364 with a more moderate depth. For example, the depth may be about 0.5 to about 3 millimeters or less for these applications.

As shown in FIG. 8, assembly 310 may be used to retrieve filter 24. According to this embodiment, tapering member 312 (i.e., segments 362) can expand to the enlarged second position. Expansion ability may be enhanced by manufacturing tapering member 312 from a more flexible material. When in the second position, sheath 14 can be advanced over filter 24 until filter 24 is suitably contained within sheath 14. It can also be appreciated that assembly 310 can also be used to deliver filter 24. For example, filter 24 may be disposed within sheath 14 as shown in FIG. 8 and then advanced to an area or interest. Once positioned, sheath 14 can then be retracted from filter 24, allowing filter to assume an expanded configuration suitable for filtering embolic debris.

Figure 9:
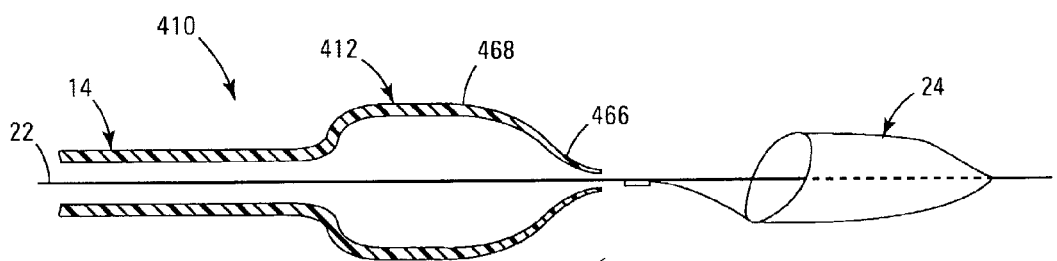
FIG. 9 is a partial cross-sectional view of another example of an embolic protection delivery and/or retrieval assembly.

FIG. 9 is a partial cross-sectional view of another example retrieval and/or delivery assembly 410. Assembly 410 is essentially the same as assembly 10, except that tapering member 412 includes a flexible distal tip portion 466 with a filter housing portion 468. In some embodiments, however, tapering member 412 may not include housing portion 468. According to this embodiment, distal tip portion 466 may be generally disposed at distal end 16 of sheath 14.

Figure 10:
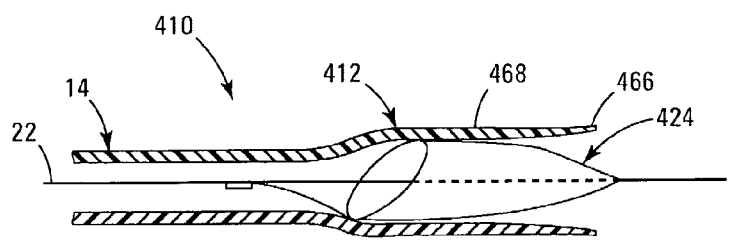
FIG. 10 is a partial cross-sectional view of the assembly of FIG. 9, wherein the sheath is configured for having an embolic protection filter disposed therein.
Figure 11:
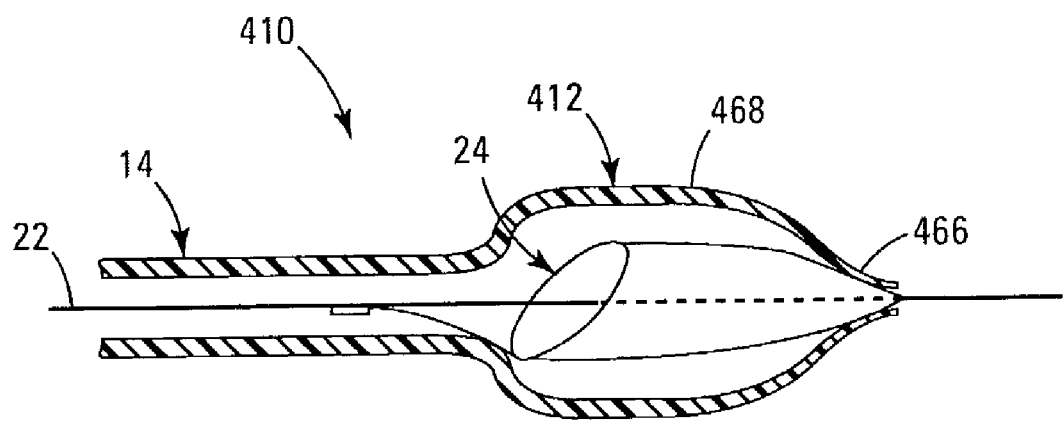
FIG. 11 is a partial cross-sectional view of the assembly of FIG. 9, wherein the filter is disposed within the sheath.

Tapering member 412 may be adapted and configured to shift between the first position and the second position analogous to the positions described above. Shifting to the second position may result in distal tip portion 466 expanding as shown in FIG. 10. According to this embodiment, distal tip portion 466 is comprised of a flexible material. Tapering member 412 may begin to shift when sheath 14 is advanced until a portion of filter 24 (e.g., strut 32) contacts distal tip portion 466. Tip 466 then expands to a size sufficient for filter 24 to become disposed therein as sheath 14 is further advanced. Once filter 24 is sufficiently enclosed within tapering member 412 (e.g., enclosed within housing portion 468), distal tip portion 466 may shift back to the first position as shown in FIG. 11.

Figure 12:
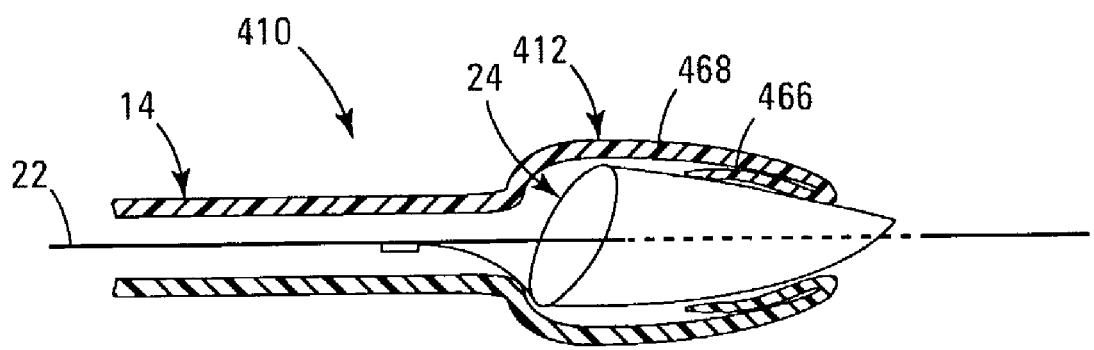
FIG. 12 is a partial cross-sectional view of the assembly of FIG. 9, wherein the sheath is shifted to a second position according to an alternative mechanism.

FIG. 12 illustrates an alternative shifting mechanism for assembly 410. According to this embodiment, distal tip portion 466 may fold back proximally as sheath 14 is advanced over filter 24. Folding back distal tip portion 466 provides sufficient space for filter 24 to be disposed within housing portion 468 of tapering member 412.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An embolic protection filter assembly, comprising:
   an outer sheath having a proximal end, a distal end, a lumen extending therethrough and a central longitudinal axis;
   an elongate shaft disposed in at least a portion of the lumen, the shaft having a distal end;
   an embolic protection filter coupled to the shaft near the distal end thereof;
   wherein a housing region is defined at the distal end of the sheath, the housing region including a housing lumen that is sized to accommodate the filter therein;
   a tapering member coupled to the sheath and disposed near the distal end of the sheath, the tapering member being adapted and configured to shift between a first position and a second position, such that when the tapering member is in the first position, the tapering member provides the outer sheath with a tapered distal tip;
   wherein the tapering member includes a notched tip disposed at the distal end of sheath, the notched tip including a plurality of segments having a plurality of notches disposed therebetween; and
   wherein the plurality of segments is biased towards the central longitudinal axis in the first position.

2. The assembly of claim 1, further comprising a marker member coupled to the sheath.

3. The assembly of claim 1, wherein the segments are formed of a flexible material.

4. An embolic protection filter assembly, comprising:
   a sheath having a proximal end, a distal end, a lumen extending therethrough, and a central longitudinal axis;
   a guidewire disposed in at least a portion of the lumen, the guidewire having a distal end;
   an embolic protection filter coupled to the guidewire near the distal end thereof;
   wherein a housing region is defined at the distal end of the sheath, the housing region including a housing lumen that is sized to accommodate the filter therein;
   a tapering member coupled to the sheath and disposed near the distal end of the sheath; and
   wherein the tapering member is adapted and configured to shift between a first position wherein at least a portion of the tapered region is disposed at the distal end of the sheath and a second position, and wherein the tapering member includes a flexible notched tip disposed at the distal end of sheath, the notched tip including a plurality of segments having a plurality of notches disposed therebetween, wherein the plurality of segments is biased towards the central longitudinal axis in the first position.

5. The assembly of claim 4, further comprising a marker member coupled to the sheath.

6. The assembly of claim 4, wherein tapering member includes a flexible tip having a flexible tapered tip portion.

7. The assembly of claim 6, wherein the tip portion is configured to expand when the tapering member shifts to the second position.

8. The assembly of claim 6, wherein the tip portion is configured to fold back proximally when the tapering member shifts to the second position.

9. The assembly of claim 1, wherein the plurality of notches narrow distally when the tapering member is in the first position.

* * * * *